United States Patent [19]

Stoller

[11] 4,263,744
[45] Apr. 28, 1981

[54] METHOD OF MAKING COMPOST AND SPAWNED COMPOST, MUSHROOM SPAWN AND GENERATING METHANE GAS

[76] Inventor: Benjamin B. Stoller, P.O. Box 1339, Santa Cruz, Calif. 95060

[21] Appl. No.: 66,623

[22] Filed: Aug. 15, 1979

[51] Int. Cl.³ .............................................. A01B 33/02
[52] U.S. Cl. ...................................................... 47/1.1
[58] Field of Search ......................................... 47/1.1

[56] References Cited

U.S. PATENT DOCUMENTS 2,723,493  11/1955  Stoller ..................................... 47/1.1
2,994,160   8/1961  Sinden et al. ............................ 47/1.1
3,704,752  12/1972  Piacentino .......................... 47/1.1 X Primary Examiner—Robert E. Bagwill
Attorney, Agent, or Firm—Robert G. Slick

[57] ABSTRACT

An improved method for making composts, aerating composts, growing mushroom spawn, generating methane gas and filling conveyors in the mushroom-growing industry is provided using ribbon-type mixers. The mixers may be of the double-ribbon type for purely mixing operations and of the single-ribbon type for operations wherein it is primarily desired to move the material from one place to another. All of the mixers are equipped to operate under pressure.

6 Claims, 4 Drawing Figures

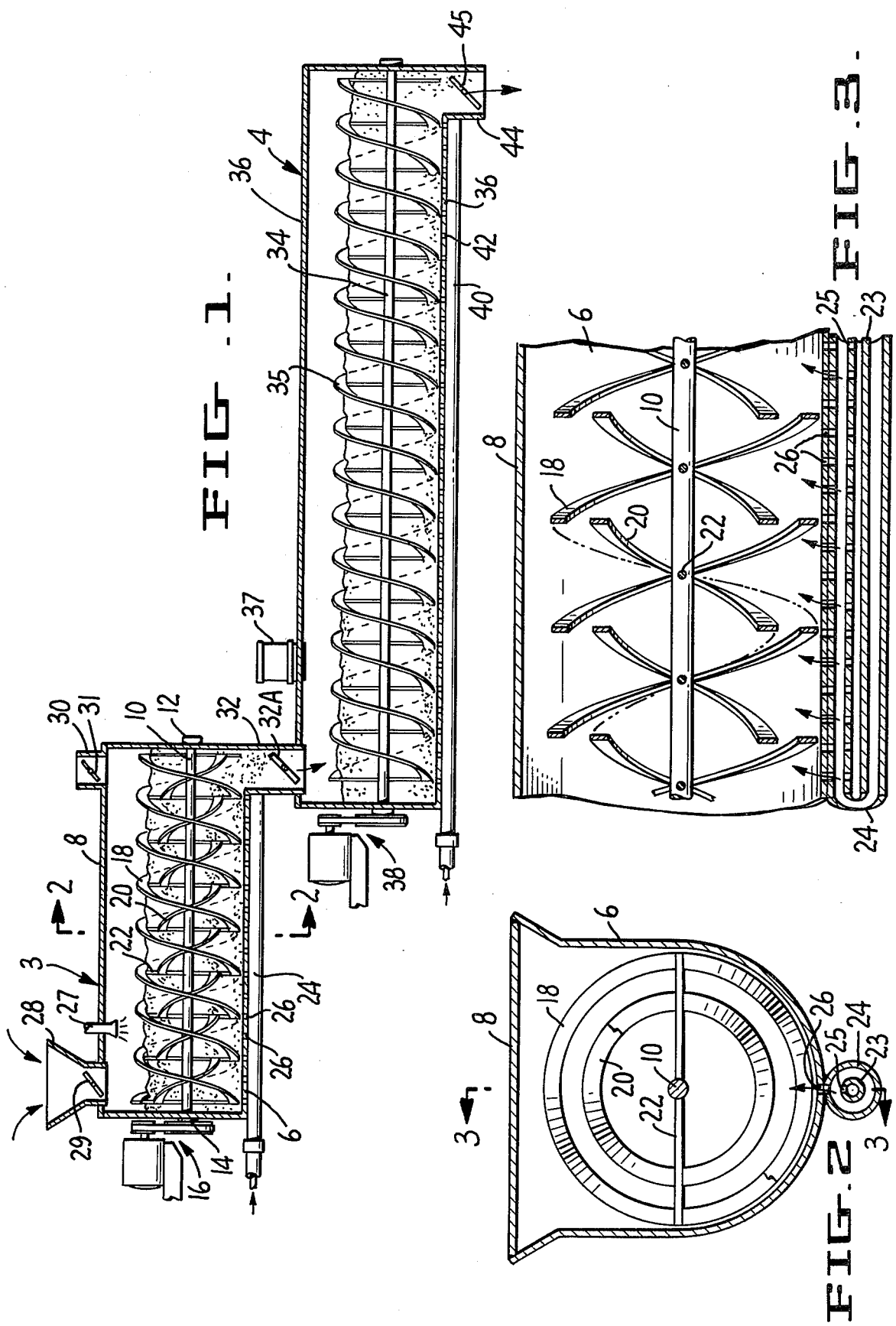

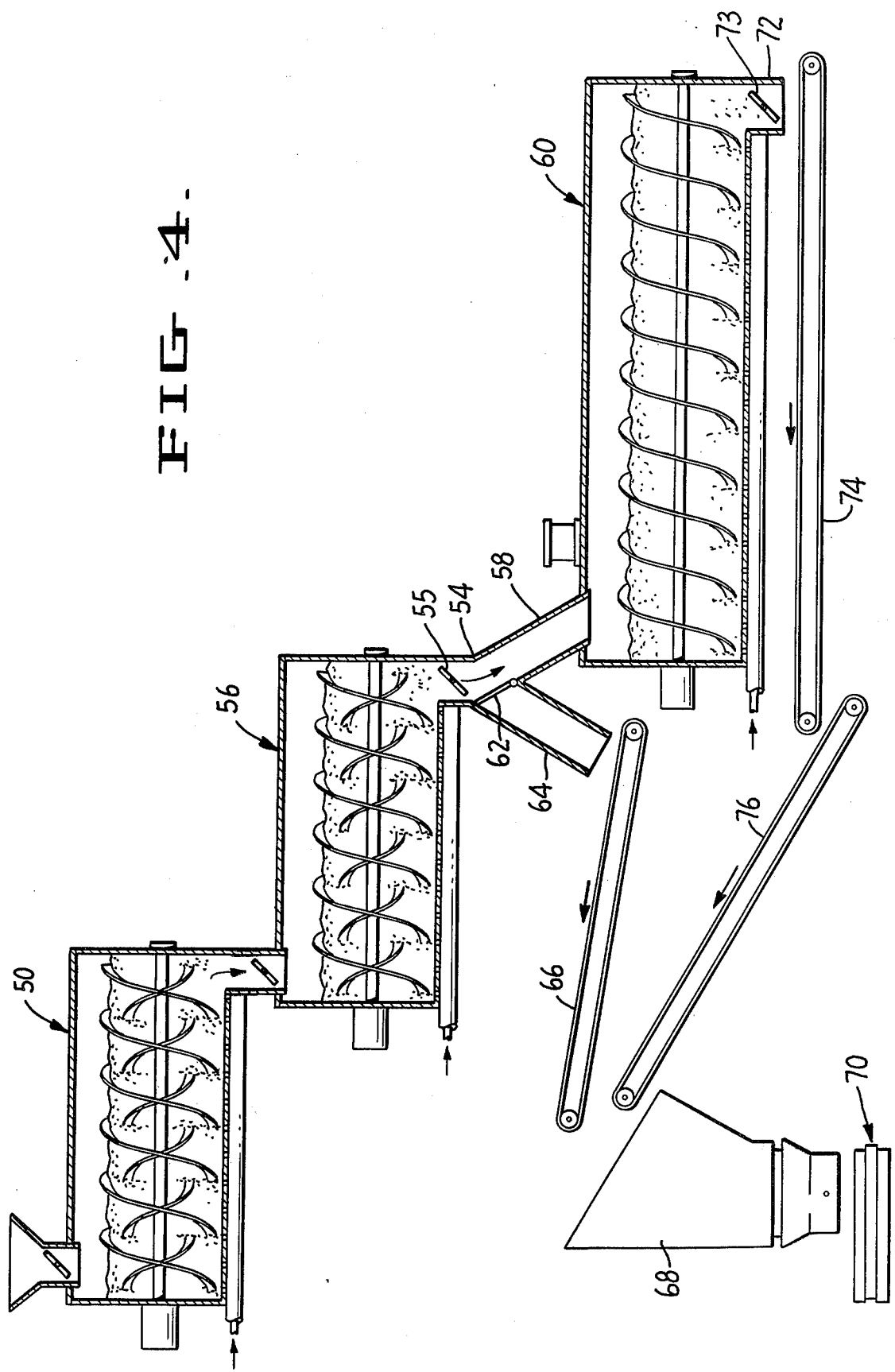

METHOD OF MAKING COMPOST AND SPAWNED COMPOST, MUSHROOM SPAWN AND GENERATING METHANE GAS

SUMMARY OF THE INVENTION

The present method is an improvement on my prior U.S. Pat. No. 2,723,493. In this prior patent I disclosed and claimed methods for making bulk composts, including ventilated floors for aeration of composts, the growing of spawn and the use of such equipment for conveying the compost material and filling trays.

In the growing of mushrooms, it is necessary to start with a compost which is homogeneous with respect to microbial decomposition of cellulosic, organic materials. The compost must be uniform with respect to the distribution of inorganic and organic ingredients, moisture and acidity. Further, undesirable microflora and insects must be destroyed by a rapid thermophilic fermentation.

In my prior U.S. Pat. No. 2,723,493 I showed how this could be accomplished using various mixing devices utilized in the mushroom industry. The results have not been fully satisfactory, although this was a distinct advance in the art.

In the past, the mixers used have been of the traveling type wherein the mixer moves back and forth over a row of material. The disadvantage of the traveling-type mixer is that it is expensive and slow besides not affording the thorough mixing so that air, water, steam and refrigerated air can easily and quickly penetrate completely the mass of the compost.

A further disadvantage of the mixers heretofore used is that they are very difficult to clean. If microbes are left in the mixer, diseases, and in particular sporeless hardcap, can be induced into subsequent batches of mushrooms.

A further disadvantage of the methods heretofore used is that they are relatively slow so that the mixing takes a long period of time. In contrast, the mixing method of the present invention operates in a very rapid fashion.

Another disadvantage as described in my previous patent is the difficulty in removal of compost from the compartment or mixer. Workers have to enter the compartment, equivalent to space of mixer, in order to effect removal of material. Contamination of all kinds is possible in this case. On the other hand, with ribbon mixers, the area of the mixer is easily and expeditiously emptied without entry of workers, thus removing this source of contamination.

Although ribbon blenders or mixers have been used in other process industries for many years, they have not heretofore been used in the preparation of mushroom compost, despite the fact that the industry for many years has sought improved methods of making and blending compost.

The ribbon blenders used in the course of the present invention may have a single ribbon of steel about 3 inches wide and about ⅜ to ⅝ inches thick wound around a driven shaft which revolves within a horizontal drum or partial drum with a clearance of about ⅛ inch. Such a blender with its spiral ribbon effectively serves not only to blend material but also to empty the mixer. Such blenders ordinarily have a diameter of from 8 to 15 feet, and they are ordinarily at least 20 feet long. They have a closable shell so that they can operate under pressure.

Other types of ribbon blenders are the split ribbon blender and the double ribbon blender, the latter having two helical ribbons, one within the other, and wound in opposite directions; that is, a right hand and a left hand ribbon. In addition, blenders having a split ribbon wherein the hand of the ribbon changes near the center can also be employed. Such mixers tend to convey the material to the center if one desires a central discharge of material.

Thus, the present invention provides a method of (1) efficiently and quickly mixing compost, circulating and composting materials, (2) excellent penetration through the mass of compost of air, steam, water, fumigants and nutrients (3) conveying of such materials from the mixer into a desired location such as growing trays. Thus, the advantages of the present invention can be summed up as follows:

A. Improved mixing with double ribbon blender. Thorough mixing of the ingredients is essential.

The thorough, continuous mixing by ribbons removes the necessity of a perforated floor for aeration as described in my previous patent. A perforated floor is very expensive and requires considerable space. The aeration can be with pipes and holes in bottom of mixer, and then air diffused all through mixer by the ribbon-mixing device.

B. A considerable difficulty is presented in removal of material from the mixer chamber. The method as described in my previous patent requires a very large chamber and slow, costly equipment.

By use of a single ribbon the material can be very expeditiously be moved in one direction. Of course, a double ribbon can also be used and material removed as it approaches one end. But a single ribbon is preferable in spawning, so that a continuous area is spawned as spawn is added.

C. Aeration is greatly simplified, since air may be admitted from one of several pipes, with holes in bottom of mixer. The same holes and pipes can also be used to admit steam for heating, water for additional moisture and refrigerated air for cooling and entrance of fumigants or gaseous nutrients. However, several pipes are preferable.

D. Composting and growth of spawn is faster under a pressurized enclosure. Accordingly, this mixing equipment is ideally suitable for admission of air under pressure. Accordingly, the advanges of this process are:
1. A double ribbon for mixing.
2. A simple method for aerating, watering, steaming and cooling compost in mixer, which eliminates expensive perforated floors.
3. A simple method for removal of compost by use of a single or double ribbon.
4. The use of single ribbon in a continuous process, where materials are introduced at one end and removed at other end.
5. Pressurized air for rapid composting and fast spawn growth.

Various other features and advantages of the invention will be brought out in the balance of the specification.

BRIEF DESCRIPTION OF THE DRAWINGS

FIG. 1 is a side view, partly in section, showing two modified ribbon mixers operating in accordance with the present invention.

FIG. 2 is an enlarged section on the line 2—2 of FIG. 1.

FIG. 3 is a section on the line 3—3 of FIG. 2.

FIG. 4 is a sectional view of an improved mixing and conveying scheme.

DESCRIPTION OF THE PREFERRED EMBODIMENTS

The general function and the description of the parts will first be set forth and thereafter specific examples of carrying out typical processes will be set forth in detail.

The operations of composting, fermenting or spawn growing can be carried out as a batch process in which case the apparatus shown in FIGS. 1-3 is suitable. These processes can also be carried out on a continuous basis in which case the apparatus shown in FIG. 4 is suitable. Normally, for a single operation such as pasteurizing composts and spawning, the equipment shown in FIGS. 1-3 is entirely adequate and in some instances only the first mixer is used. Of course, as is later explained in detail, the equipment shown in FIG. 4 can also be used for this purpose by employing only the first one or first two mixers.

Referring now to FIGS. 1-3, a suitable mixer generally designated 3 has a cylindrical shell 6 having a gas tight top cover 8. A shaft 10 supported on bearings 12 and 14 runs through the center of the semicylindrical section, the shaft being driven by a suitable motor and coupling generally designated 16. Shaft 10 supports an outer ribbon 18 and an inner ribbon 20 by means of the radial arms 22. It will be seen that the two ribbons have a helical configuration and that the outer ribbon 18 forms a close fit with the lower half of the cylindrical shell 6. It will also be seen that the two helical ribbons are of opposite hands. In the examples shown, the outer ribbon 18 is in the form of a right-hand thread and the inner ribbon 20 is in the form of a left-hand thread although, of course, the situation could be reversed. At the bottom of the shell 6 are concentric pipes 23 and 24 having a plurality of openings, respectively 25 and 26, extending from the pipes, the latter opening into the interior of the shell. Air, steam, gaseous nutrients, and/or fumigants from sources not shown, can be introduced into these pipes to aerate, heat, moisten, fumigate or fertilize the mixture. It is preferable to have separate pipes for steam and air as shown; however, air and steam can be introduced alternately with a timing device.

At one end of the shell 6 is a funnel-like opening 28 having closure 29 to which material can be introduced and at the opposite end is an opening 30 having closure 31 in the upper cover 8 of the shell for pressure or vacuum. Regulators and/or gages, not illustrated, may be employed for temperature and $CO_2$ control. Openings 28 and 30 are provided with closing devices 29 and 31, respectively, so that the mixer can operate under pressure. Pipe 27 is used to introduce water into the mixer, as an alternate entry. At the bottom of the shell is an outlet 32 having closure 32A for the discharge of the solid material.

Outlet 32 discharges into a second ribbon mixer generally designated 4, and this is similar to the ribbon mixer 3 except that it has only a single ribbon so that there is mixing action only at the entry, as for spawning, and a greater conveying action. In other words, with the double ribbon mixer 3, the outer ribbon 18 has a substantially greater area in contact with material within the mixer than the inner ribbon 20. Thus, as the ribbon 20 attempts to convey the material in one way, the outer ribbon 18 tends to convey it in the opposite direction resulting in a tumbling and mixing action but with some conveying action by the dominant ribbon 18. In contrast, the single-ribbon mixer 4 does not have as much tumbling action but acts more or less as a gentle mixer and as a conveyor. Since the parts are quite similar to those previously described, they are described in less detail. Thus, the mixer 4 has a shell which has a closable opening 37 as well as a center shaft 34 which revolves in shell 36 by means of the drive 38. A tube 40 runs along the bottom of the shell 36 and has a plurality of openings 42 for the introduction of air or steam. A shaft 34 carries a single ribbon 35 on arms 43. A discharge 44 having a closing valve 45 is provided at the end of the mixer.

In another example of practicing the invention, compost was pasteurized in a pasteurizing room and the pasteurized compost introduced into the blender with spawn to make spawned compost. This is done at room temperature (70° F.) under air pressure of about 5 psig. In still another example, an anaerobic fermentation was conducted with compost containing a moisture of 75% to 90%

For conducting the operations of pasteurizing and spawning, this equipment is entirely adequate. The materials would be merely introduced into the opening 28, pasteurized in mixer 3 and discharged through the opening 32 into mixer 4 wherein spawn is introduced in opening 37. After spawn growth, the material is discharged through opening 44.

Referring now to FIG. 4 by reference characters, there is shown first a double-ribbon mixer generally designated 50 which feeds into another double-ribbon generally designated 56. These mixers are substantially the same as those designated 3 and 4 in FIGS 1-3 and are therefore not described in detail. Mixer 56 has a discharge chute 54 with closure 55 leading into a third ribbon mixer generally designated 60. Mixer 56 is a double-ribbon mixer and can be of the same structure as mixer 50 while mixer 60 is a single-ribbon mixer of substantially the same structure as mixer 52.

In many instances, it might be desirable to operate the equipment shown in FIG. 4 as a batch process as previously described in which case discharge outlet 54 can be provided with a diverting vane 62 so that discharge can be taken through a chute 64. A conveyor 66 can be provided under chute 64 to convey material to hopper 68 whereupon it can be used to fill trays 70.

The mixer 60 has a discharge opening 72 with closure 73 where the material can be discharged onto a conveyor 74 which can lead to conveyor 76 and thence into hopper 68. Thus, for simple operations, the two stage mixer of FIGS. 1-3 or the first half of the equipment shown in FIG. 4 may be employed while the entire apparatus of FIG. 4 can advantageously be employed for a continuous operation.

The following working examples show preferred embodiments of typical batch and continuous runs:

Batch Process

The compost is prepared outside and is then introduced in mixer 3 for pasteurizing and for making a homogeneous mixture. After filling mixer 3, water is introduced on top from 28, or may be forced by pressure from pipes 24 in bottom, as allowed for air and steam. The material is mixed as it is watered, to obtain a uniform moisture throughout of 65% to 75%. Air is introduced at the same time; the amount of air is regulated by the temperature, as the temperature rises to 140° to 160° F. more and more air is introduced. If the temperature fails to rise rapidly or to hasten the pasteurizing, steam may be introduced until these temperatures are attained. The air admitted may be pressurized to 2 to 20 lbs. pressure.

The mixing, watering, aeration and steaming are all continued until compost is grown over with actinomycetis (fire-fang), moisture about 70% odor free, and free of ammonia. Pasteurizing for 2 to 6 days should be sufficient. The length of pasteurizing will depend not only on nature of the ingredients, but also on the speed or rapidity and continuity of turning the compost. Also, the moisture of the compost must be equated with the speed of turning. For example, if the ribbon blenders revolve continuously 15 times a minute and moisture of the compost is 70%, the material can be reduced in size in a few hours. Accordingly, the moisture content at start is reduced to 50% or even less, until a thermophilic fermentation is initiated. Then the moisture content is increased, the number of revolutions is reduced to 2 per minute, and the blender blades are turned intermittently, but to maintain aerobic conditions. The number of variables are considerable: the kinds of ingredients -oats, wheat, rye, straw, etc., moisture, number of revolutions and continuity of mixing. The primary concern is for a homogeneous compost upon which the spawn will grow rapidly and produce a big crop. Conditions are altered as to composition of compost, and aeration, steaming and watering to obtain these results.

After the pasteurizing is completed (2 to 6 days), and temperature of compost is reduced to 70°-75° F., the compost in mixer 3 is discharged into mixer 4. At the front end of mixer 4, spawn is introduced in this single blade mixer. The spawn is introduced in one end and continues all along as it is mixed and conveyed by single ribbon. The mixer is turned very slowly, so that the spawn is not disturbed too much from growing. Or the mixers can be turned faster initially to empty mixer 3 of compost, and to permeate the entire compost with spawn in mixer 4. Then mixer 4 can be turned slowly or intermittently so as to allow spawn to grow without breaking up mycelium. The mixer may be made long enough to retain 1 to 4 days of spawned compost. Under pressurized aeration the spawn grows much faster. So that the spawn will grow throughout the compost in a few days. After compost is full or nearly full of spawn growth, it is removed by conveyor to trays for the growing rooms.

ECONOMY IN USE OF MIXERS

The compost, after pasteurizing and cooling to 70° to 75° F., can be spawned directly in the same mixer, i.e., mixer 3. Therein, the spawn may be allowed to grow in the same mixer with little or no mixing for a few days under pressurized air. Then the compost that is now permeated with spawn, may be removed by conveyors, not shown, to trays for completion of spawn growth or reuniting broken up mycelium caused in transferring, and subsequently for casing of spawn compost and producing mushrooms. Also, after pasteurizing and spawning, the compost may be immediately transferred to trays for growth of spawn in trays. In this practice, there is economy of using only one mixer.

In order to make mixer 3 immediately available for a new batch of compost for fermentation and/or pasteurizing, the compost may be immediately transferred into mixer 4. The compost will be spawned in mixer 4 as it leaves mixer 3. Then the spawn can be allowed to grow for several days under pressurized air. Thereafter the spawned compost is removed to trays as described above. In this practice, mixer 3 is available for a new batch, and the spawn can continue to grow in mixer 4 under pressurized air.

Continuous Process

The raw ingredients for preparing a compost for mushroom growing, namely straw or manure-straw, and various supplements as developed for mushroom growing, are inserted in mixer 50. Water is added through piping and holes in top of mixer, as required to obtain a water content of 70% to 75%. Air is admitted at bottom, and also steam to raise temperature for a thermophilic fermentation, namely to 140° to 170° F. The heat may be allowed to develop by microbial action or steam may be introduced to raise temperature to this range. Air is admitted and $CO_2$ is removed to allow for an aerobic fermentation. The air may be pressurized from 2 to 20 lbs. pressure for rapid composting.

The material is slowly turned, approximately one turn per minute, to give a thorough mixing action. However, the speed of turning may be increased to 5 to 15 revolutions per minute in order to reduce the size of the straw length or make more intimate contact of ingredients. Faster turning can produce a quicker composting period, even reduced to hours instead of days. The mixing, to this effect, can also be done rapidly at first, then reduced subsequently to continue the aerobic fermentation. The material is sampled for percentage of water and loss of dry weight. In 3 to 6 days the dry weight loss should be 15% to 30%, and the color of the material, a dark brown. Free ammonia may be present. After appropriate dry weight loss and moisture content, the material is removed to mixer 56.

In mixer 56 the temperature is maintained at 140° to 160° F., depending on the type of supplements added to the straw, which is the usual practice in making composts for mushroom growing. The moisture is adjusted to 70% to 75%, and the material is mixed as described previously. Air is admitted, preferably under pressure, to obtain a rapid aerobic pasteurizing. Accordingly, carbon dioxide must be exhausted to maintain aerobic conditions.

After a temperature of 140° to 160° F. has been maintained for several days, the temperature is reduced to 125° to 130° F. In this way, the compost is made free of ammonia, which is toxic to spawn growth. Pressurized air is employed as previously. After the compost is free of ammonia, the temperature is reduced by refrigerated air to 70°-75° F.

The material is then removed to mixer 60. Spawn is introduced at one end of the mixer, and then spawn is mixed by the single blade throughout the compost and conveyed to the other end. The material is allowed to grow under pressurized air at 75° F. for several days. Then the spawned compost is removed to trays on a conveyor for casing and growing mushrooms in growing rooms.

Methane Gas Production

The same equipment may be used in a preliminary anaerobic fermentation to obtain methane gas; then the fermentation can be changed over to aerobic, in order to make a compost for mushroom growing. A two-stage fermentation of this kind actually occurs in the compost pile when preparing manure-straw substrates for making composts for mushroom growing: The inner part of the compost pile, where $CO_2$ may build up to 21% or higher, and also methane is produced, is anaerobic, whereas the outside layer of the pile, about 6 to 12 inches thick, is full of grey-speckled "fire-fang" or actinomycetes fungi, which are an indication of, and which can only grow under, aerobic conditions. But in our process, the anaerobic is completely separated from the aerobic by a two-stage operation, as in the blender. In this way we recover the methane gas, which is today a very valuable source of energy needed to fire our boilers. Then, after recovering the methane, we switch over to an aerobic process for making mushroom compost.

To introduce a preliminary anaerobic stage prior to the aerobic in our equipment, the method is to employ a pressurized reducing atmosphere, instead of the oxidizing atmosphere as characterized by oxygen. To produce a reducing atmosphere for anaerobic growth, the atmosphere should consist of inert gases such as nitrogen, or reducing gases such as hydrogen sulfide, methane, $CO_2$ or combinations of these and other substances. Also, the gases produced from previous anaerobic fermentation, which consist of methane, $CO_2$, and $H_2S$, may be used. Then, when most of the methane has been derived from the compost, the atmosphere is changed over to an oxidizing one by introducing air or oxygen under pressure. Of course, the preliminary anaerobic stage may be skipped and only an aerobic stage used.

In the anaerobic fermentation the moisture of the compost should be approximately 75%. This moisture is also suitable for mushroom compost. However, if more methane gas can be generated by increasing the moisture to 80%–85%, then hot air drying will have to be introduced when changing over to aerobic fermentation.

The constituents of the compost may be altered, especially if the methane fermentation precedes the aerobic fermentation. For example, the amount of gypsum may be reduced or eliminated because it may serve as a source of sulfur from which hydrogen sulfide is formed. On the other hand, the gypsum, which is a good deflocculating agent, may be introduced after the anaerobic fermentation is finished; in this way the gypsum will deflocculate the wet compost as may occur under anaerobic conditions. Other agents and substances may be used as substitutes for gypsum.

The air-tight ribbon blender also affords the possibility of adding a gaseous nutrient such as ammonia gas; this ammonia is the most economical source of nitrogen available. The ammonia gas may also serve as a fumigant. Other fumigants that may be used are formaldehyde, propylene oxide, and combinations of above or others.

The purpose of fumigation is to reduce the time required for pasteurizing and to prevent the degrading of valuable nutrients. Accordingly, more food will be available for growth of mushroom mycelium and subsequently mushrooms. Fumigation also serves to help reducing the time of blending, which has tendency to reduce the size of the particles of the compost. The fermentation is standardized for a specific kind of ingredient, for different sources of ingredients, for different kinds of microbial inoculums, and for different pasteurizing procedures, by establishing a relationship between the loss in dry weight of the compost, and the increase in percent ash, to the temperature in the compartment and the carbon dioxide in the exhaust air. When the loss in dry weight is 15% to 30%, the fermentation is considered completed, although the percentage can vary greatly from this range, especially when non-fermentable ingredients are used, or a specific organism is inoculated or is induced to predominate.

I claim:

1. The method of composting, mixing, pasteurizing and aerating mixtures of raw compost and making spawned compost mixtures, including the generation of methane, comprising the steps of:
   a. providing a ribbon mixer, said ribbon mixer having a shaft mounted for rotation therein, said shaft supporting a double helical spiral, said mixer having means for introducing steam and/or air along the bottom and having means for introducing water at the top of the mixer, said mixer being enclosed whereby it can be operated at a selected pressure and temperature;
   b. introducing into said mixer a mixture selected from raw compost and compost with spawn;
   c. agitating said material in said ribbon mixer by revolving said shaft while adding water and/or steam thereto to maintain the contents of said mixture at a selected temperature; and
   d. discharging the resulting mixture from said mixer.

2. The method of claim 1 wherein pressurized air is introduced into said mixer.

3. The method of claim 1 wherein a nutrient is introduced into said mixer.

4. The method of claim 1 wherein a fumigant is introduced said mixer.

5. The method of composting, mixing, pasteurizing and aerating mixtures of raw compost and making spawned compost mixtures, including the generation of methane, comprising the steps of:
   a. providing a ribbon mixer, said ribbon mixer having a shaft mounted for rotation therein, said shaft supporting a double helical spiral, said mixer having means for introducing steam and/or air along the bottom and having means for introducing water thereto at the top of the mixer, said mixer being enclosed whereby it can be operated at a selected pressure and temperature;
   b. introducing into said mixer a mixture selected from raw compost and compost with spawn;
   c. agitating said material in said ribbon mixer by revolving said shaft while adding water and/or steam thereto to maintain the contents of said mixture at a selected temperature; and
   d. discharging the resulting mixture from said mixer into a second ribbon mixer said second ribbon mixer having an enclosed connection to the first mixer and having a shaft mounted for rotation therein, said shaft supporting a single helical spiral, said mixer having means for introducing steam and/or air through along the bottom, said second mixer being enclosed, whereby both mixers can be operated at a selected pressure and temperature;
   e. permitting said mixture to reside in said second mixer to continue processing for a substantial period of time, and
   f. discharging the finished product from the second mixer.

6. The method of claim 5 having in addition thereto a third ribbon mixer whereby a first double-ribbon mixer feeds a second ribbon mixer and said second ribbon mixer discharges into a single ribbon mixer.

* * * * *